(12) United States Patent
Hirokawa et al.

(10) Patent No.: US 12,737,911 B2
(45) Date of Patent: Sep. 15, 2026

(54) DEVICE AND METHOD FOR IMAGE PROCESSING INCLUDING VASCULAR IMAGE PROCESSING

(71) Applicant: NIKON CORPORATION, Tokyo (JP)

(72) Inventors: Mariko Hirokawa, Yokohama (JP); Yasushi Tanabe, Fujisawa (JP); Takahiko Yoshida, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 455 days.

(21) Appl. No.: 17/919,037

(22) PCT Filed: Mar. 8, 2021

(86) PCT No.: PCT/JP2021/009001

§ 371 (c)(1), (2) Date: Oct. 14, 2022

(87) PCT Pub. No.: WO2021/210295

PCT Pub. Date: Oct. 21, 2021

(65) Prior Publication Data

US 2023/0237684 A1 Jul. 27, 2023

(30) Foreign Application Priority Data

Apr. 15, 2020 (JP) ................................ 2020-073123

(51) Int. Cl.
*G06T 7/62* (2017.01)
*A61B 3/10* (2006.01)
(Continued)

(52) U.S. Cl.
CPC ................ *G06T 7/62* (2017.01); *A61B 3/102* (2013.01); *G06T 7/0014* (2013.01); *G06T 7/66* (2017.01);
(Continued)

(58) Field of Classification Search
CPC ........... G06T 7/62; G06T 7/0014; G06T 7/66; G06T 2207/10101; G06T 2207/30041;
(Continued)

(56) References Cited

U.S. PATENT DOCUMENTS 9,713,424 B2 * 7/2017 Spaide ................ A61B 3/1233
10,136,812 B2 11/2018 Yasuno et al.
(Continued)

FOREIGN PATENT DOCUMENTS

WO WO-2016/103484 A1 6/2016
WO WO-2016/103489 A1 6/2016
(Continued)

OTHER PUBLICATIONS

Joshi, Vinayak S., et al. "Automated method for identification and artery-venous classification of vessel trees in retinal vessel networks." PloS one 9.2 (2014): e88061. (Year: 2014).*
(Continued)

*Primary Examiner* — Henok Shiferaw
*Assistant Examiner* — Dion J Satcher
(74) *Attorney, Agent, or Firm* — Foley & Lardner LLP

(57) ABSTRACT

An image processing method performed by a processor and including: a step of acquiring a choroidal vascular image; a step of detecting a vortex vein position from the choroidal vascular image; a step of identifying a choroidal vessel related to the vortex vein position; and a step of finding a size of the choroidal vessel.

8 Claims, 15 Drawing Sheets

(51) Int. Cl.

| | |
|---|---|
| ***G06T 7/00*** | (2017.01) |
| ***G06T 7/66*** | (2017.01) |
| ***G06V 40/14*** | (2022.01) |
| ***G06V 40/18*** | (2022.01) |

(52) U.S. Cl.
CPC ............ *G06V 40/14* (2022.01); *G06V 40/193* (2022.01); *G06T 2207/10101* (2013.01); *G06T 2207/30041* (2013.01); *G06T 2207/30101* (2013.01)

(58) Field of Classification Search
CPC .......... G06T 2207/30101; A61B 3/102; A61B 3/0033; A61B 3/0041; A61B 3/0025; A61B 3/12; G06V 40/14; G06V 40/193
USPC .......................................................... 382/131
See application file for complete search history.

(56) References Cited

U.S. PATENT DOCUMENTS

| | | | | |
|---|---|---|---|---|
| 2007/0086637 | A1* | 4/2007 | Zhang | G06T 7/0012 382/131 |
| 2009/0046251 | A1 | 2/2009 | Peyman et al. | |
| 2016/0022369 | A1* | 1/2016 | Audigier | G09B 23/30 434/268 |
| 2016/0166141 | A1 | 6/2016 | Kanagasingam et al. | |
| 2016/0284085 | A1* | 9/2016 | Huang | G06T 7/136 |
| 2017/0035286 | A1* | 2/2017 | Meyer | A61B 3/1233 |
| 2017/0347881 | A1 | 12/2017 | Noda | |
| 2017/0347882 | A1 | 12/2017 | Noda | |
| 2019/0014982 | A1* | 1/2019 | Bhuiyan | G06T 7/44 |
| 2019/0274538 | A1* | 9/2019 | Imamura | A61B 3/1241 |
| 2020/0020100 | A1* | 1/2020 | Kyriakou | G06T 7/12 |
| 2020/0237213 | A1* | 7/2020 | Ono | G06V 40/193 |
| 2020/0394789 | A1* | 12/2020 | Freund | G06T 7/0012 |
| 2021/0004939 | A1 | 1/2021 | Hirokawa | |
| 2021/0022600 | A1 | 1/2021 | Tanabe et al. | |
| 2021/0022606 | A1 | 1/2021 | Tanabe et al. | |
| 2021/0224980 | A1* | 7/2021 | Yang | G06T 7/0012 |

FOREIGN PATENT DOCUMENTS

| | | | | |
|---|---|---|---|---|
| WO | WO-2019/181981 | A1 | 9/2019 | |
| WO | WO-2019/203311 | A1 | 10/2019 | |
| WO | WO-2019203309 | A1 * | 10/2019 | G16H 30/40 |

OTHER PUBLICATIONS

Japanese Office Action issued in corresponding Japanese Patent Application No. 2022-515242, dated Sep. 17, 2024 (5 pages).

JP Office Action issued in corresponding Japanese Patent Application No. 2025-082129 Dated Dec. 16, 2025 (6 pages).

Japanese Notice of Refusal issued in Japanese Patent Application No. 2025-082129 dated Jul. 7, 2026, with Machine Translation (5 pages).

* cited by examiner

FIG.1

100
110
OPHTHALMIC DEVICE
130
140
150

110
16
CONTROL DEVICE
CPU
RAM
ROM
16A
16B
16C
16E
INPUT/DISPLAY DEVICE
16D
I/O
16F
COMMU-NICATION I/F
17
IMAGE PROCESSING DEVICE
14
20
OCT UNIT
20A
LIGHT SOURCE
20B
SENSOR
20C
20D
20E
20F
19
IMAGING OPTICAL SYSTEM
22
OPTICAL SCANNER
30
WIDE-ANGLE OPTICAL SYSTEM
SLO UNIT
18
40
42
44
46
B LIGHT SOURCE
G LIGHT SOURCE
R LIGHT SOURCE
R LIGHT SOURCE
48
50
52
54
56
62
60
58
64
76
IR LIGHT DETECTOR
74
R LIGHT DETECTOR
72
G LIGHT DETECTOR
70
B LIGHT DETECTOR
27
12
12A
O
Y
Z
X

FIG.3

254
STORAGE DEVICE
140
262
CPU
270
268
266
RAM
I/O
264
ROM
DISPLAY
256
255M
255K
252
COMMUNICATION I/F
258
130

DISPLAY CONTROL SECTION

204

IMAGE PROCESSING CONTROL SECTION

206

PROCESSING SECTION

DEVICE AND METHOD FOR IMAGE PROCESSING INCLUDING VASCULAR IMAGE PROCESSING

CROSS-REFERENCE TO RELATED APPLICATIONS

This application is a National Stage of International Application No. PCT/JP2021/009001, filed Mar. 8, 2021, the disclosure of which is incorporated herein by reference in its entirety. Further, this application claims priority from Japanese Patent Application No. 2020-073123, filed Apr. 15, 2020, the disclosure of which is incorporated herein by reference in its entirety.

TECHNICAL FIELD

Technology disclosed herein relates to an image processing method, an image processing device, and a program.

BACKGROUND ART

Technology for analyzing blood vessels of a choroid has hitherto been proposed (specification of U.S. patent Ser. No. 10/136,812).

There is a desire to analyze choroidal vessels at a vortex vein periphery.

SUMMARY OF INVENTION

A first aspect of technology disclosed herein is image processing performed by a processor and including: a step of acquiring a choroidal vascular image; a step of detecting a vortex vein position from the choroidal vascular image; a step of identifying a choroidal vessel related to the vortex vein position; and a step of determining a size of the choroidal vessel.

An image processing device of a second aspect of technology disclosed herein includes a memory and a processor connected to the memory, wherein the processor executes: a step of acquiring a choroidal vascular image; a step of detecting a vortex vein position from the choroidal vascular image; a step of identifying a choroidal vessel related to the vortex vein position; and a step of determining a size of the choroidal vessel.

A program of a third aspect of technology disclosed herein causes a computer to execute: a step of acquiring a choroidal vascular image; a step of detecting a vortex vein position from the choroidal vascular image; a step of identifying a choroidal vessel related to the vortex vein position; and a step of determining a size of the choroidal vessel.

BRIEF DESCRIPTION OF DRAWINGS

FIG. 1 is a schematic configuration diagram of an ophthalmic system of an exemplary embodiment.

FIG. 3 is a schematic configuration diagram of a server.

FIG. 4 is an explanatory diagram of functions implemented by an image processing program in a CPU of a server.

FIG. 6 is a flowchart illustrating image processing by a server.

DESCRIPTION OF EMBODIMENTS

Figure 1:
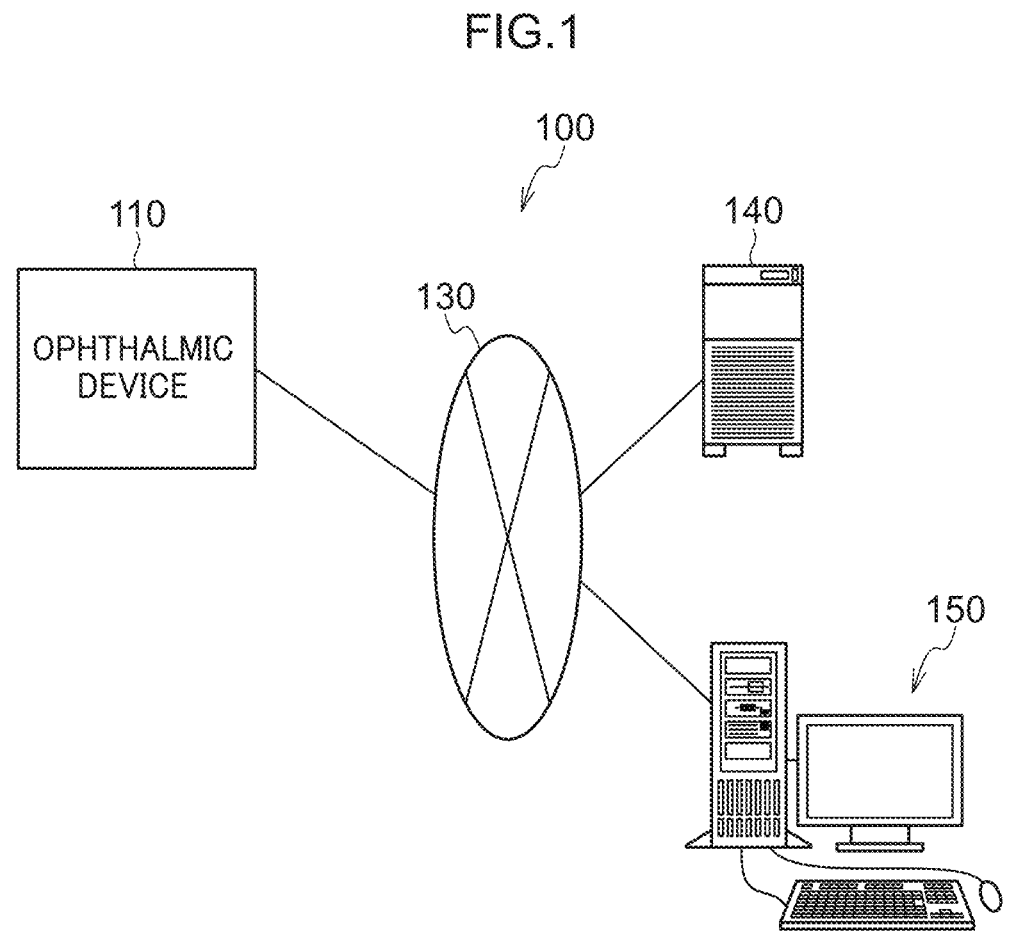
Figure 2:
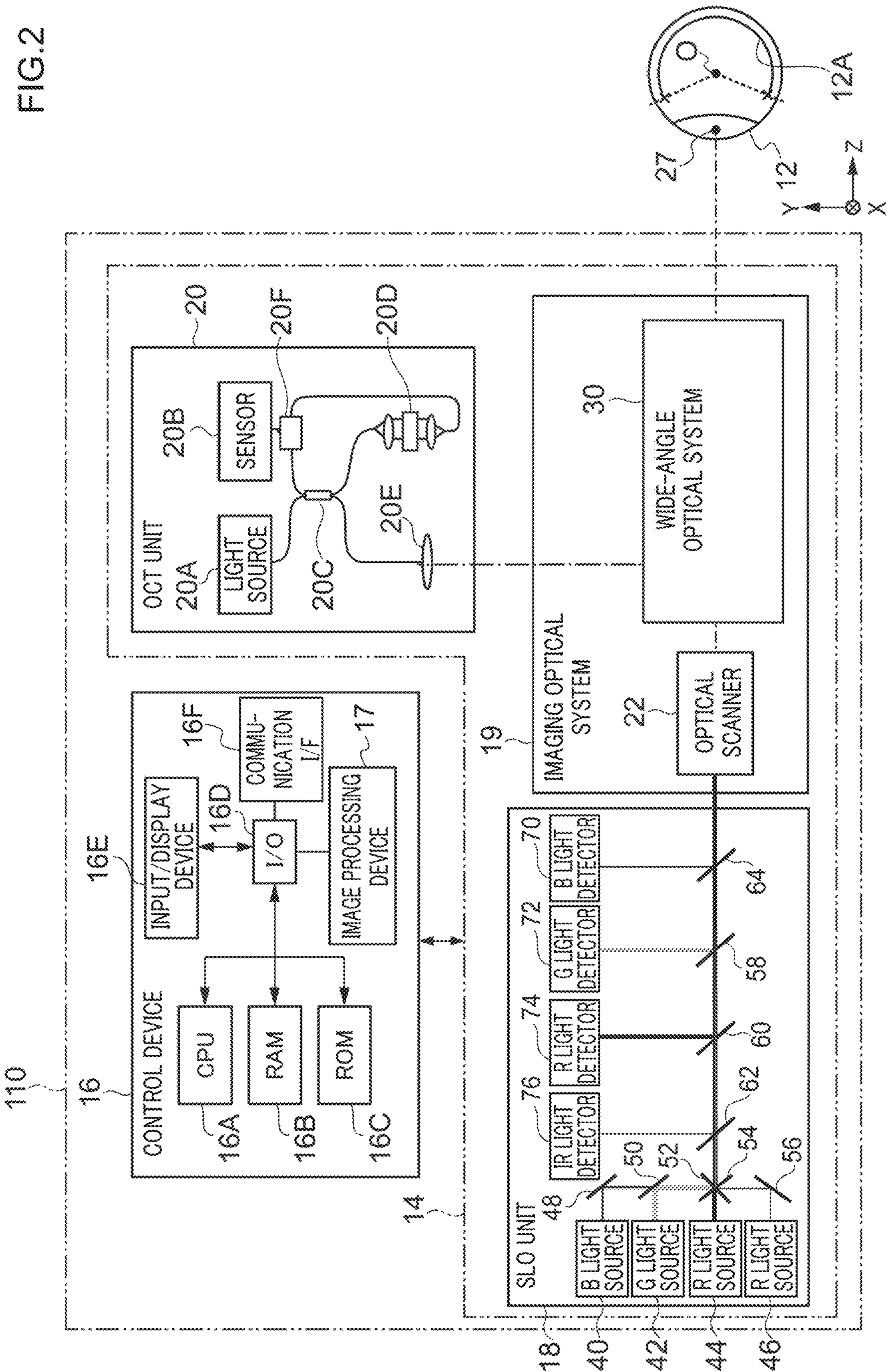
FIG. 2 is a schematic configuration diagram of an ophthalmic device of the present exemplary embodiment.

Explanation follows regarding an ophthalmic system 100 according to an exemplary embodiment of the present invention, with reference to the drawings. FIG. 1 illustrates a schematic configuration of the ophthalmic system 100. As illustrated in FIG. 1, the ophthalmic system 100 includes an ophthalmic device 110, a server device (referred to hereafter as "server") 140, and a display device (referred to hereafter as "viewer") 150. The ophthalmic device 110 acquires fundus images. The server 140 stores plural fundus images obtained by imaging the fundi of plural patients using the ophthalmic device 110 and eye axial lengths measured by a non-illustrated eye axial length measurement device, in association with patient IDs. The viewer 150 displays fundus images and analysis results acquired by the server 140.

The server 140 is an example of an "image processing device" of technology disclosed herein.

The ophthalmic device 110, the server 140, and the viewer 150 are connected together through a network 130. The viewer 150 is a client in a client-server system, and plural such devices are connected together through a network. There may also be plural devices for the server 140 connected through the network in order to provide system redundancy. Alternatively, if the ophthalmic device 110 is provided with image processing functionality and with the image viewing functionality of the viewer 150, then the fundus images may be acquired and image processing and image viewing performed with the ophthalmic device 110 in a standalone state. Moreover, if the server 140 is provided with the image viewing functionality of the viewer 150, then the fundus images may be acquired and image processing and image viewing performed by a configuration of the ophthalmic device 110 and the server 140.

Note that other ophthalmic equipment (examination equipment for measuring a field of view, measuring intraocular pressure, or the like) and/or a diagnostic support device that analyzes images using artificial intelligence (AI) may be connected to the ophthalmic device 110, the server 140, and the viewer 150 over the network 130.

Next, explanation follows regarding a configuration of the ophthalmic device 110, with reference to FIG. 2.

For ease of explanation, scanning laser ophthalmoscope is abbreviated to SLO. Moreover, optical coherence tomography is abbreviated to OCT.

With the ophthalmic device 110 installed on a horizontal plane and a horizontal direction taken as an X direction, a direction perpendicular to the horizontal plane is denoted a Y direction, and a direction connecting the center of the pupil at the anterior eye portion of the examined eye 12 and the center of the eyeball is denoted a Z direction. The X direction, the Y direction, and the Z direction are thus mutually perpendicular directions.

The ophthalmic device 110 includes an imaging device 14 and a control device 16. The imaging device 14 is provided with an SLO unit 18, and an OCT unit 20, and acquires a fundus image of the fundus of the examined eye 12. Two-dimensional fundus images that have been acquired by the SLO unit 18 are referred to as SLO images. Tomographic images, face-on images (en-face images) and the like of the retina created based on OCT data acquired by the OCT unit 20 are referred to as OCT images.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input/display device 16E connected to the CPU 16A through the I/O port 16D. The input/display device 16E includes a graphical user interface to display images of the examined eye 12 and to receive various instructions from a user. An example of the graphical user interface is a touch panel display.

The control device 16 is also provided with an image processing device 17 connected to the I/O port 16D. The image processing device 17 generates images of the examined eye 12 based on data acquired by the imaging device 14. Note that the control device 16 is connected to the network 130 through a communication interface 16F.

Although the control device 16 of the ophthalmic device 110 is provided with the input/display device 16E as illustrated in FIG. 2, the technology disclosed herein is not limited thereto. For example, a configuration may adopted in which the control device 16 of the ophthalmic device 110 is not provided with the input/display device 16E, and instead a separate input/display device is provided that is physically independent of the ophthalmic device 110. In such cases, the display device is provided with an image processing processor unit that operates under the control of a display control section 204 of the CPU 16A in the control device 16. Such an image processing processor unit may be configured so as to display SLO images and the like based on an image signal output as an instruction by the display control section 204.

The imaging device 14 operates under the control of the CPU 16A of the control device 16. The imaging device 14 includes the SLO unit 18, an imaging optical system 19, and the OCT unit 20. The imaging optical system 19 includes an optical scanner 22 and a wide-angle optical system 30.

The optical scanner 22 scans light emitted from the SLO unit 18 two dimensionally in the X direction and the Y direction. As long as the optical scanner 22 in an optical element capable of deflecting light beams, it may be configured by any out of, for example, a polygon mirror, a mirror galvanometer, or the like. A combination thereof may also be employed.

The wide-angle optical system 30 combines light from the SLO unit 18 with light from the OCT unit 20.

The wide-angle optical system 30 may be a reflection optical system employing a concave mirror such as an elliptical mirror, a refraction optical system employing a wide-angle lens, or may be a reflection-refraction optical system employing a combination of a concave mirror and a lens. Employing a wide-angle optical system that utilizes an elliptical mirror, wide-angle lens, or the like enables imaging to be performed not only of a central portion of the fundus, but also of the retina at the fundus periphery.

For a system including an elliptical mirror, a configuration may be adopted that utilizes an elliptical mirror system as disclosed in International Publication (WO) Nos. 2016/103484 or 2016/103489. The disclosures of WO Nos. 2016/103484 and 2016/103489 are incorporated in their entirety in the present specific by reference.

Observation of the fundus over a wide field of view (FOV) 12A is implemented by the wide-angle optical system 30. The FOV 12A refers to a range capable of being imaged by the imaging device 14. The FOV 12A may be expressed as a viewing angle. In the present exemplary embodiment the viewing angle may be defined in terms of an internal illumination angle and an external illumination angle. The external illumination angle is the angle of illumination by a light beam shone from the ophthalmic device 110 toward the examined eye 12, and is an angle of illumination defined with respect to a pupil 27. The internal illumination angle is the angle of illumination of a light beam shone onto the fundus F, and is an angle of illumination defined with respect to an eyeball center O. Correspondence relationships exists between the external illumination angle and the internal illumination angle. For example, an external illumination angle of 120° is equivalent to an internal illumination angle of approximately 160°. The internal illumination angle in the present exemplary embodiment is 200°.

SLO fundus images obtained by imaging at an imaging angle having an internal illumination angle of 160° or greater are referred to as UWF-SLO fundus images. UWF is an abbreviation of ultra-wide field (ultra-wide angled). A region extending from a posterior pole portion of a fundus of the examined eye 12 past an equatorial portion thereof can be imaged by the wide-angle optical system 30 having a field of view (FOV) angle of the fundus that is an ultra-wide field, enabling imaging of structural objects, such as vortex veins, present at fundus peripheral portions.

An SLO system is realized by the control device 16, the SLO unit 18, and the imaging optical system 19 as illustrated in FIG. 2. The SLO system is provided with the wide-angle optical system 30, enabling fundus imaging over the wide FOV 12A.

The SLO unit 18 is provided with a blue (B) light source 40, a green (G) light source 42, a red (R) light source 44, an infrared (for example near infrared) (IR) light source 46, and optical systems 48, 50, 52, 54, 56 to guide the light from the light sources 40, 42, 44, 46 onto a single optical path using reflection or transmission. The optical systems 48, 56 are mirrors, and the optical systems 50, 52, 54 are beam splitters. B light is reflected by the optical system 48, is transmitted through the optical system 50, and is reflected by the optical system 54. G light is reflected by the optical systems 50, 54, R light is transmitted through the optical systems 52, 54, and IR light is reflected by the optical systems 52, 56. The respective lights are thereby guided onto a single optical path.

The SLO unit 18 is configured so as to be capable of switching between the light sources for emitting laser light of different wavelengths or a combination of the light sources, such as a mode in which R light and G light are emitted, a mode in which infrared light is emitted, etc. Although the example in FIG. 2 includes four light sources, i.e. the B light source 40, the G light source 42, the R light source 44, and the IR light source 46, the technology disclosed herein is not limited thereto. For example, the SLO unit 18 may, furthermore, also include a white light source, in a configuration in which light is emitted in various modes, such as a mode in which G light, R light, and B light is emitted, and a mode in which white light is emitted alone.

Light introduced to the imaging optical system 19 from the SLO unit 18 is scanned in the X direction and the Y direction by the optical scanner 22. The scanning light passes through the wide-angle optical system 30 and the pupil 27 and is shone onto the fundus. Reflected light that has been reflected by the fundus passes through the wide-angle optical system 30 and the optical scanner 22 and is introduced into the SLO unit 18.

The SLO unit 18 is provided with a beam splitter 64 that, from out of the light coming from the posterior eye portion (fundus) of the examined eye 12, reflects the B light therein and transmits light therein other than the B light, and a beam splitter 58 that, from out of the light transmitted by the beam splitter 64, reflects the G light therein and transmits light therein other than the G light. The SLO unit 18 is further provided with a beam splitter 60 that, from out of the light transmitted through the beam splitter 58, reflects the R light therein and transmits light therein other than the R light. The SLO unit 18 is further provided with a beam splitter 62 that reflects IR light from out of the light transmitted through the beam splitter 60. The SLO unit 18 includes a B light detector 70 for detecting the B light reflected by the beam splitter 64, a G light detector 72 for detecting G light reflected by the beam splitter 58, an R light detector 74 for detecting R light reflected by the beam splitter 60 and an IR light detector 76 for detecting IR light reflected by the beam splitter 62.

Light that has passed through the wide-angle optical system 30 and the optical scanner 22 and been introduced into the SLO unit 18 (i.e. reflected light that has been reflected by the fundus) is reflected by the beam splitter 64 and photo-detected by the B light detector 70 when B light, and is reflected by the beam splitter 58 and photo-detected by the G light detector 72 when G light. When R light, the incident light is transmitted through the beam splitter 58, reflected by the beam splitter 60, and photo-detected by the R light detector 74. When IR light, the incident light is transmitted through the beam splitters 58, 60, reflected by the beam splitter 62, and photo-detected by the IR light detector 76. The image processing device 17 operating under the control of the CPU 16A employs signals detected by the B light detector 70, the G light detector 72, the R light detector 74, and the IR light detector 76 to generate UWF-SLO images.

The control device 16 also controls the light sources 40, 42, 44 so as to emit light at the same time. A green fundus image, a red fundus image, and a blue fundus image are obtained with mutually corresponding positions by imaging the fundus of the examined eye 12 at the same time with the B light, G light, and R light. An RGB color fundus image is obtained from the green fundus image, the red fundus image, and the blue fundus image. The control device 16 obtains a green fundus image and a red fundus image with mutually corresponding positions by controlling the light sources 42, 44 so as to emit light at the same time and by imaging the fundus of the examined eye 12 at the same time with the G light and R light. An RG color fundus image is obtained from the green fundus image and the red fundus image.

A region extending from a posterior pole portion of a fundus of the examined eye 12 past an equatorial portion thereof can be imaged by the wide-angle optical system 30 with a field of view (FOV) angle of the fundus that is an ultra-wide field.

Figure 5A:
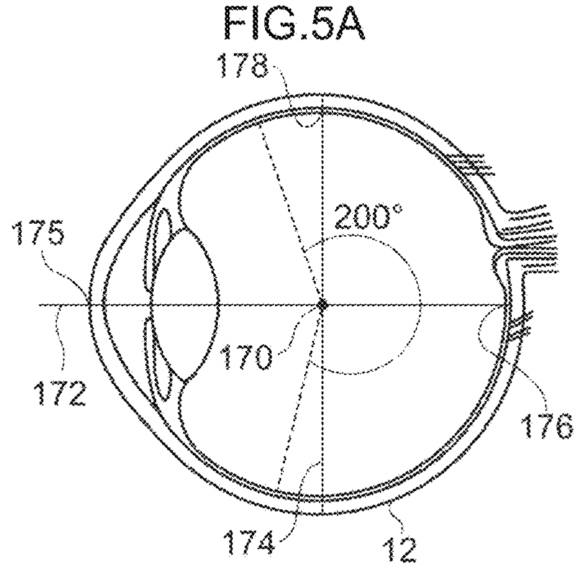
FIG. 5A is an explanatory diagram of an equatorial portion of an eyeball.

Explanation follows regarding an equatorial portion 178, with reference to FIG. 5A. The eyeball (examined eye 12) is a spherical structural object having an eyeball center 170 and a diameter of about 24 mm. A straight line connecting an anterior pole 175 thereof with a posterior pole 176 thereof is called an ocular axis 172, a line where a plane orthogonal to the ocular axis 172 intersects with the eyeball surface is referred to as a line of latitude, and the equator 174 corresponds to the line of latitude with the greatest length. A part of the retina and the choroid coinciding with the position of the equator 174 configures the equatorial portion 178.

The ophthalmic device 110 is capable of imaging a region with an internal illumination angle of 200° with respect to the eyeball center 170 of the examined eye 12 as a reference position. Note that an internal illumination angle of 200° corresponds to an external illumination angle of 110° with respect to the pupil of the eyeball of the examined eye 12 as the reference. Namely, the wide-angle optical system 30 illuminates laser light through the pupil at an angle of view for an external illumination angle of 110° in order to image a fundus region with an internal illumination angle of 200°.

Figure 5B:
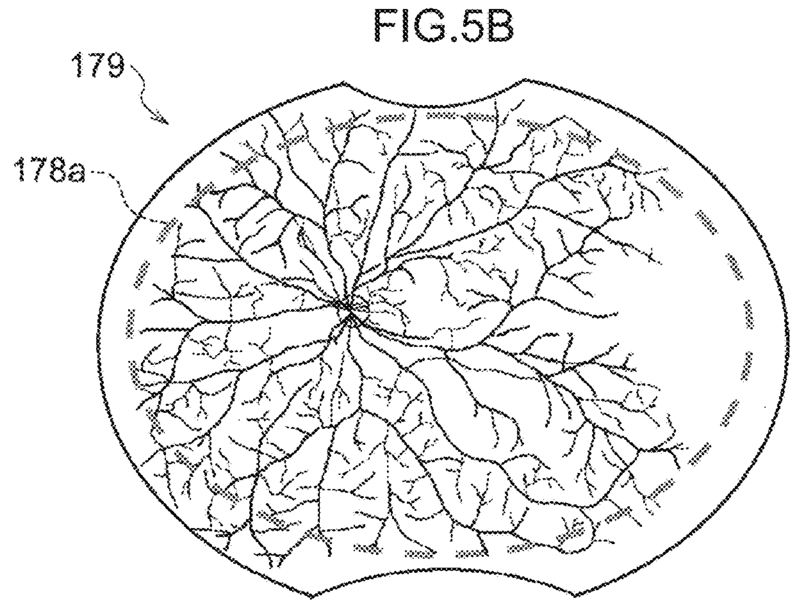
FIG. 5B is a schematic diagram illustrating a UWF-SLO image of a fundus imaged over a wide field.

FIG. 5B illustrates a UWF-SLO image 179 obtained by imaging with the ophthalmic device 110 capable of scanning with an internal illumination angle of 200°. As illustrated in FIG. 5B, the equatorial portion 178 corresponds to an internal illumination angle of 180°, and the locations indicated by the dotted line **178*a* on the UWF-SLO image 179 correspond to the equatorial portion 178. In this manner, the ophthalmic device 110 is capable of imaging a fundus region extending from a posterior pole portion past the equatorial portion 178**.

Figure 5C:
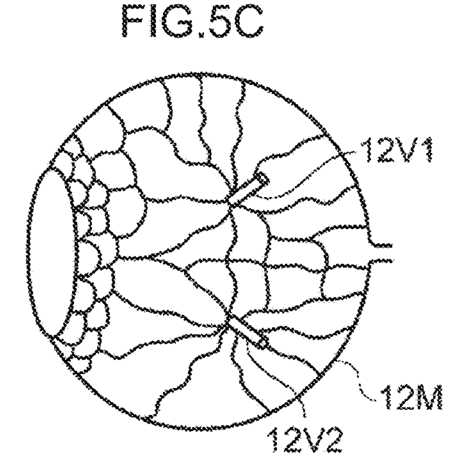
FIG. 5C is a schematic diagram illustrating a positional relationship between a choroid and vortex veins in an eyeball.

FIG. 5C is a diagram illustrating a positional relationship in an eyeball between a choroid 12M and vortex veins 12V1, V2. The mesh pattern in FIG. 5C indicates the choroidal vessels of the choroid 12M. The choroidal vessels carry blood around the entire choroid. Blood flows out from the eyeball through plural (normally four to six) vortex veins present in the examined eye 12. FIG. 5C illustrates an upper vortex vein V1 and a lower vortex vein V2 present on one side of the eyeball. Vortex veins are often present in the vicinity of the equatorial portion 178. Accordingly, the ophthalmic device 110 that is capable of scanning with the above internal illumination angle 200° is employed in order to image the vortex veins present in the examined eye 12 and the choroidal vessels peripheral to the vortex veins.

An OCT system is implemented by the control device 16, the OCT unit 20, and the imaging optical system 19 illustrated in FIG. 2. The OCT system includes the wide-angle optical system 30, and is accordingly able to perform OCT imaging of fundus peripheral portions similarly to the imaging of SLO fundus image described above. Namely, OCT imaging over a region extending from a posterior pole portion of the examined eye 12 fundus past the equatorial portion 178 is able to be performed by employing the wide-angle optical system 30 having a field of view (FOV) angle of the fundus that is an ultra-wide field. OCT data of structural objects such as vortex veins present in the fundus peripheral portions can be acquired, and tomographic images of vortex veins and a 3D structure of vortex veins can be obtained by performing image processing on the OCT data.

The OCT unit 20 includes a light source 20A, a sensor (detection element) 20B, a first light coupler 20C, a reference optical system 20D, a collimator lens 20E, and a second light coupler 20F.

Light emitted from the light source 20A is split by the first light coupler 20C. One part of the split light is collimated by the collimator lens 20E into parallel light serving as measurement light before being introduced into the imaging optical system 19. The measurement light is shone onto the fundus through the wide-angle optical system 30 and the pupil 27. Measurement light that has been reflected by the fundus passes through the wide-angle optical system 30 so as to be introduced into the OCT unit 20, then passes through the collimator lens 20E and the first light coupler 20C before being incident to the second light coupler 20F.

The other part of the light emitted from the light source 20A and split by the first light coupler 20C is introduced into the reference optical system 20D as reference light, and is made incident to the second light coupler 20F through the reference optical system 20D.

The respective lights that are incident to the second light coupler 20F, namely the measurement light reflected by the fundus and the reference light, interfere with each other in the second light coupler 20F so as to generate interference light. The interference light is photo-detected by the sensor 20B. The image processing device 17 operating under the control of an image processing section 206 generates OCT images, such as tomographic images and en-face images, based on OCT data detected by the sensor 20B.

OCT images obtained by imaging with an imaging angle of an internal illumination angle of 160° or greater, or OCT images obtained by scanning the fundus peripheral portions, are collectively referred to as UWF-OCT images. The OCT images include tomographic images of the fundus by B-scan, three-dimensional images (3D images) based on OCT volume data, and en-face images (two-dimensional images) that are cross-sections of such OCT volume data.

The image data of the UWF-OCT images is sent from the ophthalmic device 110 to the server 140 though the communication interface 16F and is stored in a storage device 254.

Note that although in the present exemplary embodiment an example is given in which the light source 20A is a wavelength swept-source OCT (SS-OCT), various types of OCT system may be employed, such as a spectral-domain OCT (SD-OCT) or a time-domain OCT (TD-OCT) system.

Figure 3:
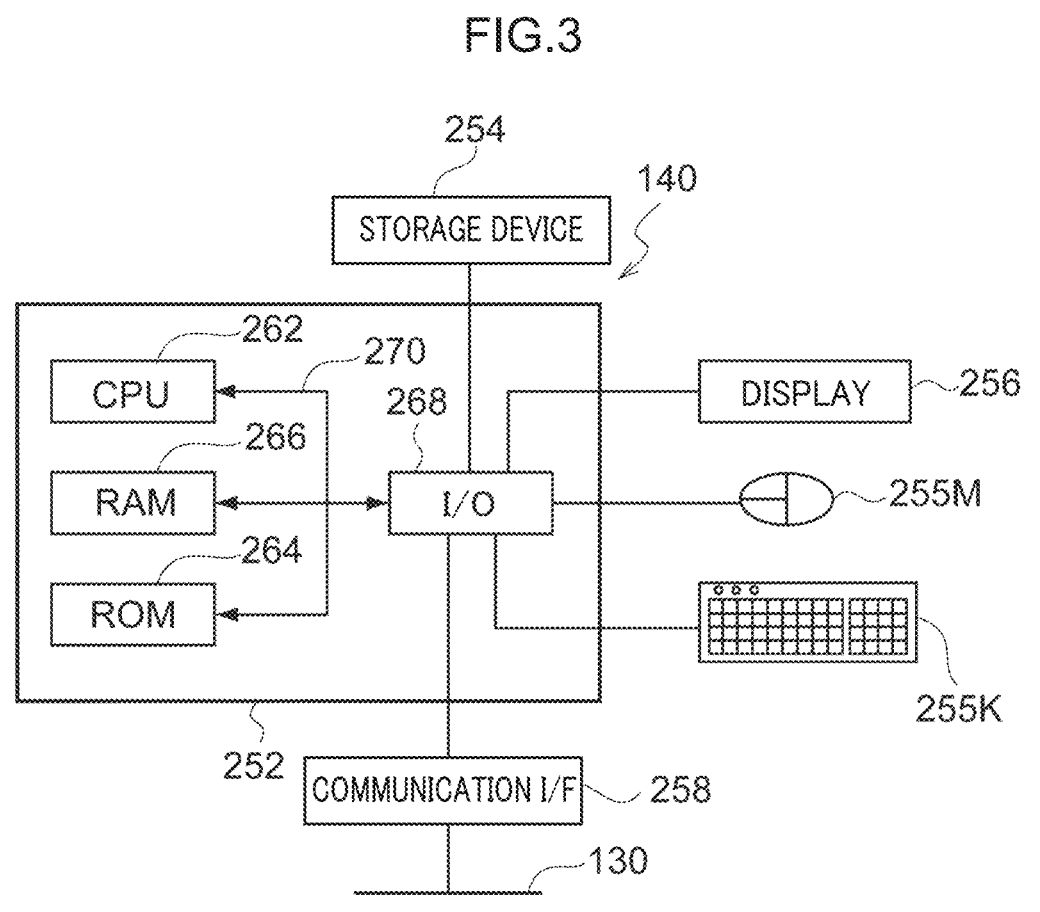

Next, explanation follows regarding a configuration of an electrical system of the server 140, with reference to FIG. 3. As illustrated in FIG. 3, the server 140 is provided with a computer body 252. The computer body 252 includes a CPU 262, RAM 266, ROM 264, and an input/output (I/O) port 268. The storage device 254, a display 256, a mouse 255M, a keyboard 255K, and a communication interface (I/F) 258 are connected to the input/output (I/O) port 268. The storage device 254 is, for example, configured by non-volatile memory. The input/output (I/O) port 268 is connected to the network 130 through the communication interface (I/F) 258. The server 140 is thus capable of communicating with the ophthalmic device 110, and the viewer 150.

Figure 6:
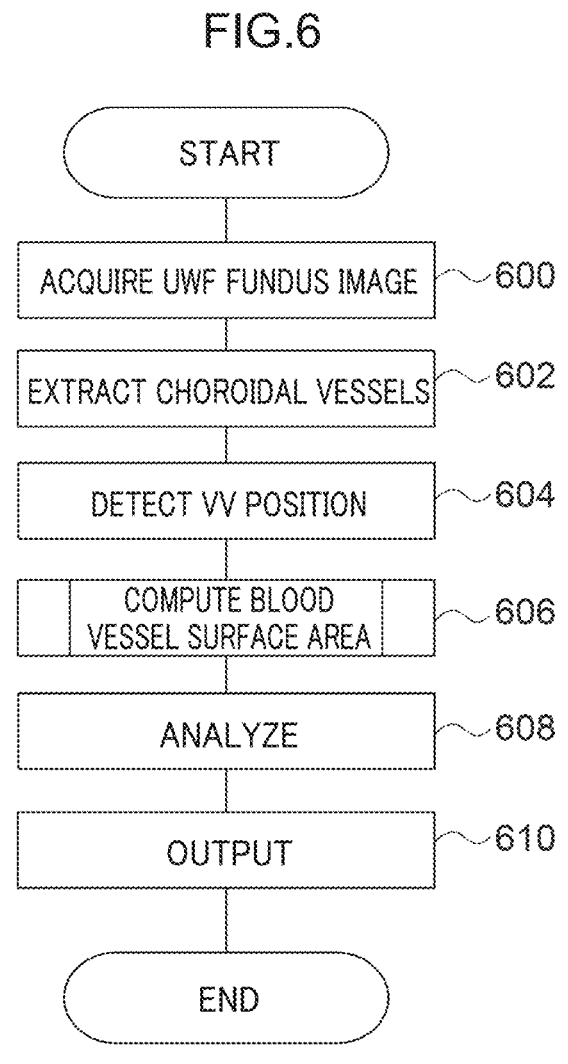

The ROM 264 or the storage device 254 is stored with the image processing program illustrated in FIG. 6.

The ROM 264 or the storage device 254 are each an example of "memory" of technology disclosed herein. The CPU 262 is an example of a "processor" of technology disclosed herein. The image processing program is an example of a "program" of technology disclosed herein.

The server 140 stores respective data received from the ophthalmic device 110 in the storage device 254.

Figure 4:
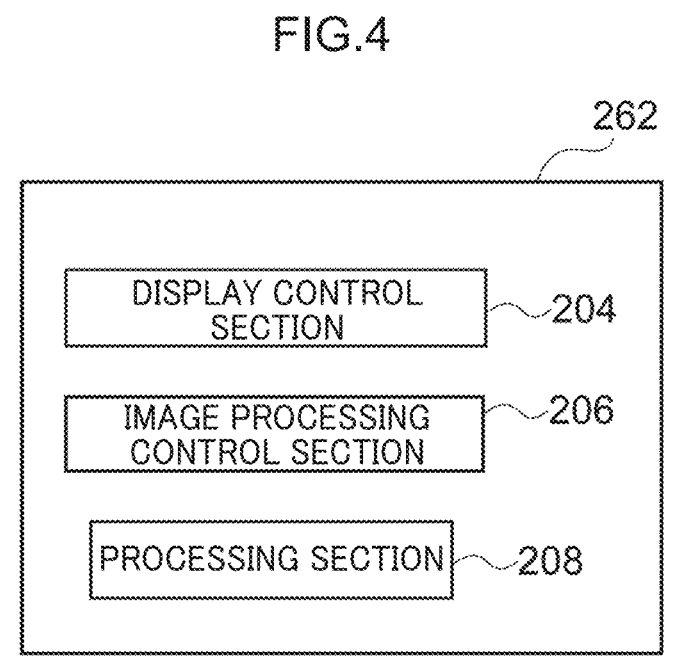

Description follows regarding various functions implemented by the CPU 262 of the server 140 executing the image processing program. The image processing program includes a display control function, an image processing function and a processing function, as illustrated in FIG. 4. By the CPU 262 executing the image processing program including each of these functions, the CPU 262 functions as a display control section 204, the image processing section 206, and a processing section 208.

Next, detailed explanation follows regarding image processing by the server 140, with reference to FIG. 6. Image processing (an image processing method) illustrated by the flowchart in FIG. 6 is implemented by the CPU 262 of the server 140 executing the image processing program.

At step 600 the image processing section 206 acquires the UWF-SLO image 179 as a UWF fundus image such as illustrated in FIG. 5B from the storage device 254. At step 602, the image processing section 206 creates (acquires) a choroidal vascular image that is an image binarized from the acquired UWF-SLO image in the following manner, and extracts the choroidal vessels from the choroidal vascular image created thereby.

First, explanation follows regarding a method for creating (acquiring) choroidal vascular images. Note that these choroidal vascular images are binarized images in which white pixels correspond to choroidal vessels and vortex veins, and black pixels correspond to other areas.

This explanation is of a case in which the choroidal vascular images are each generated from a red fundus image and a green fundus image. First, explanation follows regarding information contained in the red fundus image and the green fundus image.

The structure of an eye is one in which a vitreous body is covered by plural layers of differing structure. The plural layers include the retina, the choroid, and the sclera, listed from the most inside at the vitreous body side to the outside. R light passes through the retina to reach the choroid. The first fundus image (red fundus image) therefore contains information relating to blood vessels present within the retina (retinal vessels) and information relating to blood vessels present within the choroid (choroidal vessels). In contrast thereto, G light only reaches as far as the retina. A second fundus image (the green fundus image) accordingly only contains information relating to the blood vessels present within the retina (retinal vessels).

The image processing section 206 of the CPU 262 extracts the retinal vessels from the second fundus image (green fundus image) by applying black hat filter processing to the second fundus image (green fundus image). Next, the image processing section 206 removes the retinal vessels from a first fundus image (the red fundus image) by performing in-painting processing thereon using the retinal vessels extracted from the second fundus image (green fundus image). Namely, position information for the retinal vessels extracted from the second fundus image (green fundus image) is employed when performing processing to infill the retinal vascular structure in the first fundus image (red fundus image) using pixel values the same as those of surrounding pixels. The image processing section 206 then emphasizes the choroidal vessels in the first fundus image (red fundus image) by performing contrast limited adaptive histogram equalization (CLAHE) processing on the image data of the first fundus image (red fundus image) from which the retinal vessels have been removed. A choroidal vascular image in which the background is expressed by black pixels and the choroidal vessels are expressed by white pixels is obtained in this manner. The generated choroidal vascular image is stored in the storage device 254.

The generation of the choroidal vascular image from the first fundus image (red fundus image) and the second fundus image (green fundus image) may be performed by the image processing section 206 generating a choroidal vascular image using the first fundus image (red fundus image) or using an IR fundus image imaged with IR light.

A method to generate choroidal vascular images is disclosed in International Publication (WO) Nos. 2019-181981, the entirety of which is incorporated in the present specific by reference herein.

Next, description follows regarding a method of extracting the choroidal vessels from the choroidal vascular image.

A choroidal vascular image such as that described above is a binarized image with white pixels corresponding to choroidal vessels and vortex veins, and black pixels corresponding to other areas, and so the image processing section 206 extracts the choroidal vessels including the vortex veins by extracting portions of white pixels from the choroidal vascular image. Information of the choroidal vascular image is stored in the storage device 254. Note that vortex veins (VVs) are outflow paths for blood that has flowed into the choroid.

At step 604, a position (X,Y) of a vortex vein (VV) is detected in the following manner. The image processing section 206 sets a movement direction (blood vessel running direction) of each of the choroidal vessels in the choroidal vascular image. More specifically, first the image processing section 206 executes the following processing on each pixel in the choroidal vascular image. Namely, for each pixel the image processing section 206 sets an area (cell) having the respective pixel at the center, and creates a histogram of brightness gradient directions at each pixel of the cell. Next, the image processing section 206 takes the gradient direction having the lowest count in the histogram of each cell as the movement direction for the pixels in each of the cells. This gradient direction corresponds to the blood vessel running direction. Note that the reason for taking the gradient direction having the lowest count as the blood vessel running direction is as follows. The brightness gradient is small in the blood vessel running direction, whereas the brightness gradient is large in other directions (for example, there is a large difference in brightness between blood vessel and non-blood vessel tissue). Thus creating a histogram of brightness gradients for each of the pixels results in a small count in the blood vessel running direction. The blood vessel running direction at each of the pixels in the choroidal vascular image is set by the processing described above.

The image processing section 206 sets initial positions for M (natural number)×N (natural number) (=L) individual particles. More specifically, the image processing section 206 sets a total of L initial positions at uniform spacings on the choroidal vascular image, with M positions in the vertical direction, and N positions in the horizontal direction.

The image processing section 206 estimates (detects) the position of the vortex veins. More specifically, the image processing section 206 performs the following processing for each of the L positions. Namely, the image processing section 206 acquires a blood vessel running direction at a first position (one of the L positions), moves the particle by a specific distance along the acquired blood vessel running direction, then re-acquires the blood vessel running direction at the moved-to position, before then moving the particle by the specific distance along this acquired blood vessel running direction. This moving by the specific distance along the blood vessel running direction is repeated for a pre-set number of movement times. The above processing is executed for all L positions. Points where a fixed number of the particles or greater have congregated at this point in time are taken as the position of a vortex vein. Moreover, as an alternative vortex vein detection method, vortex vein positions may be detected by performing image processing to recognize as a vortex vein a position on a choroidal vascular image where a feature value for a radiating pattern is a specific value or greater, and a vortex vein position may be detected by detecting a vortex vein bulge portion from the choroidal vascular image. A method for detecting vortex veins is disclosed in International Publication (WO) No. 2019/203309, the entirety of which is incorporated in the present specific by reference herein.

Vortex vein position information (number of vortex veins, coordinates on the choroidal vascular image, and the like) are stored in the storage device 254.

Figure 7:
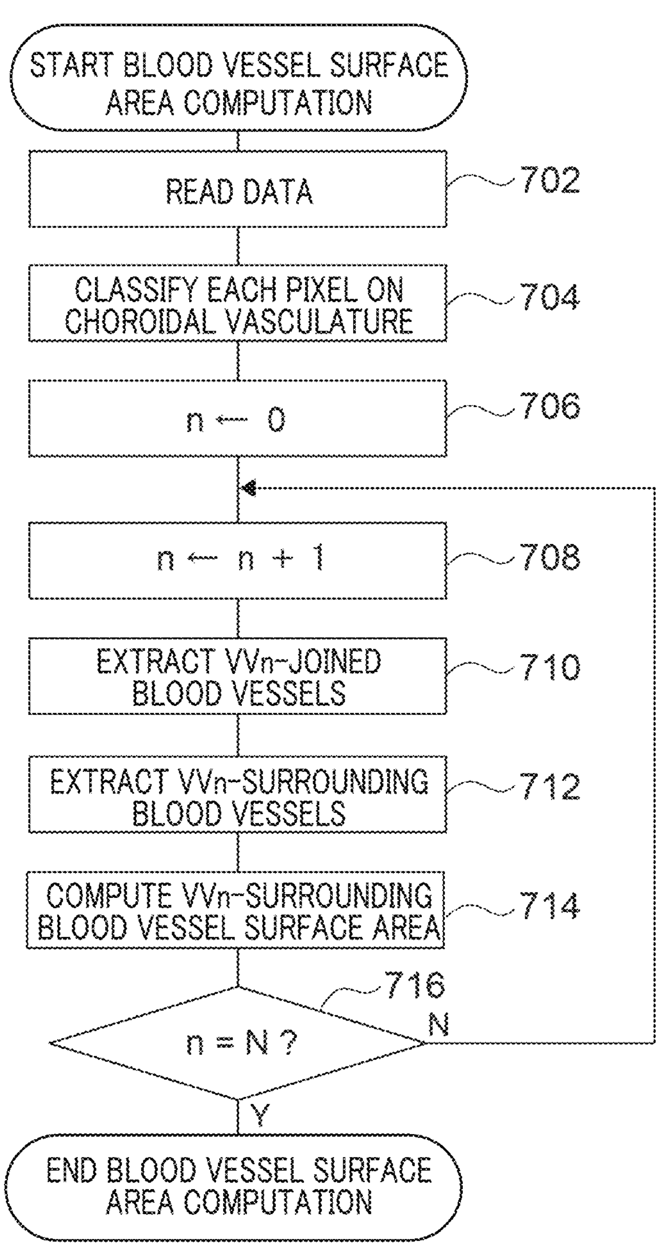
FIG. 7 is a flowchart illustrating blood vessel surface area computation processing of step 606 of FIG. 6.

At step 606, the image processing section 206 executes blood vessel surface area computation processing. FIG. 7 illustrates a flowchart indicating details of the blood vessel surface area computation processing of step 606. At step 702 of FIG. 7 the image processing section 206 reads, from the storage device 254, data of the choroidal vascular image (binarized image) and the vortex vein position information.

At step 704 the image processing section 206 performs classification of each pixel on the choroidal vessels by deciding which vortex vein (hereafter also referred to as VV) the pixel is related to from out of the plural detected VVs. Explanation follows regarding classification methods employed for each pixel on the choroidal vessels.

A first such classification method is a method for classifying by deciding boundary lines to define areas related to VVs on a choroidal vascular image. A second thereof is a method for classifying by deciding boundary points on choroidal vessels. A third thereof is a method for classifying without deciding boundary lines or boundary points. Note that an operator may use a mouse 255M or the like to set boundary lines or boundary points on the choroidal vascular image displayed on the display 256 of the server 140, or to associate pixels on the choroidal vessels with VVs thereon. However in the present exemplary embodiment, the image processing section 206 automatically classifies each of the pixels by performing image processing.

First explanation follows regarding a first classification method for classification by deciding boundary lines as mentioned above. The first classification method specifically includes a method to uniquely decide boundaries between areas related to each of the VVs in the choroidal vascular image (so as to be non-overlapping), and a method to set overlapping areas as areas related to each of the VVs.

Figure 8A:
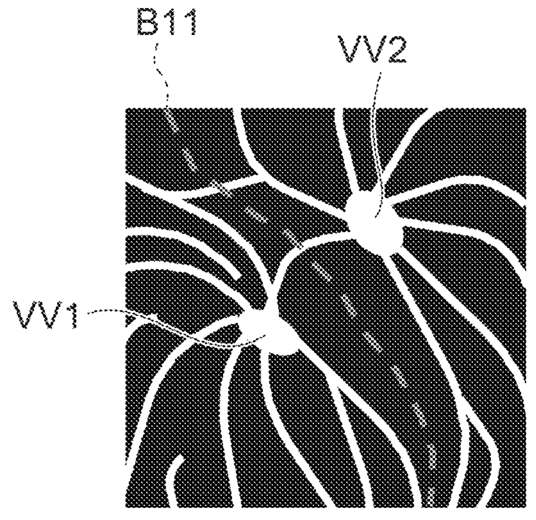
FIG. 8A is a diagram illustrating a choroidal vascular image of a part where adjacent VV1 and VV2 are present.
Figure 8B:
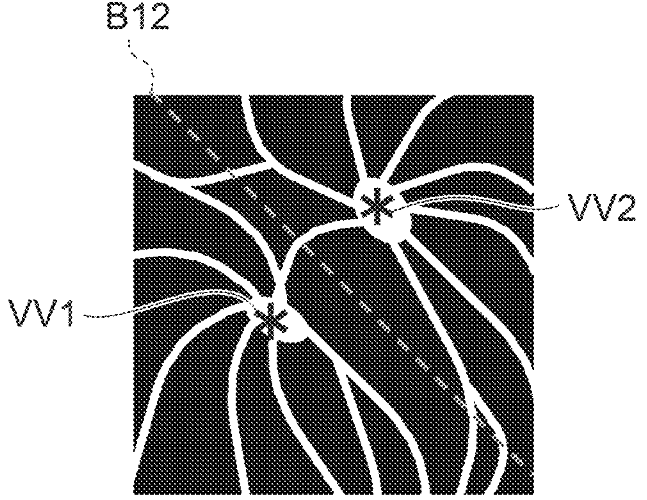
FIG. 8B is a diagram illustrating a choroidal vascular image of a part where adjacent VV1 and VV2 are present.

Explanation follows regarding the method for uniquely deciding boundaries in the first classification method. The image processing section 206 decides areas corresponding to each of the plural VVs in the choroidal vascular image so as to be adjacent to adjacent areas, namely such that no overlapping areas are generated. FIG. 8A and FIG. 8B illustrate choroidal vascular images of a part where adjacent VV1 and VV2 are present. The image processing section 206 decides a single boundary line B11 to define both an area corresponding to the VV1 and an area corresponding to the VV2, as illustrated in FIG. 8A.

Methods to decide the single boundary line B12 include, for example, a graph cut processing method. There is also the following processing method. As illustrated in FIG. 8B, the image processing section 206 computes a straight line distance from each VV for each of the pixels of the choroidal vascular image, and decides the VV that corresponds to the shortest straight line distance from the computed straight line distances, and associates each of these pixels with the decided VV. The image processing section 206 sets the pixels associated with the same VV as being in the same group. The image processing section 206 decides the single boundary line B12 so as to divide up the groups at positions between pixels where the adjacent pixels belong to different groups.

At step 704, based on the boundary line B11 or B12 the image processing section 206 decides which (just a single) VV from out of the plural VVs each of the pixels on the choroidal vessel is related to.

Figure 9A:
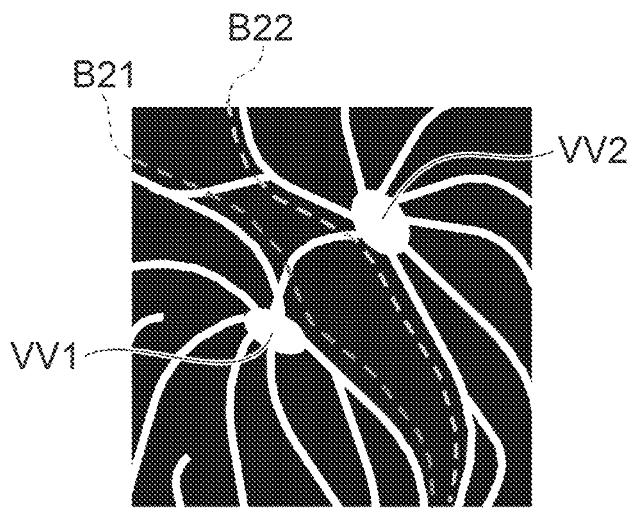
FIG. 9A is a diagram illustrating a choroidal vascular image of a part where adjacent VV1 and VV2 are present.
Figure 9B:
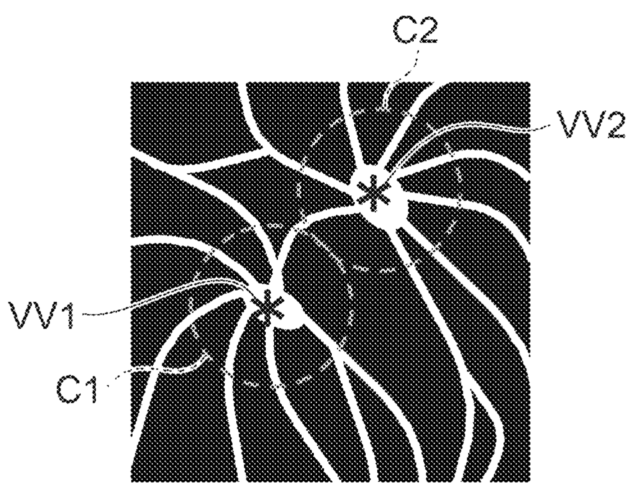
FIG. 9B is a diagram illustrating a choroidal vascular image of a part where adjacent VV1 and VV2 are present.

Explanation follows regarding a method in the first classification method for setting overlapping areas as areas related to each of the VVs. FIG. 9A and FIG. 9B illustrate a choroidal vascular image of a part where adjacent VV1 and VV2 are present. As illustrated in FIG. 9A, the image processing section 206 decides the two boundary lines B21, B22 by combining active contour processing (snakes method and level set processing). In the example illustrated in FIG. 9A, the image processing section 206 classifies each of the pixels on choroidal vessels that is positioned between the boundary lines B21, B22, and is positioned on the VV2 side of the boundary line B21 near to the VV1, as being a pixel related to the VV2. The image processing section 206 classifies each of the pixels on choroidal vessels that is positioned between the boundary lines B21, B22, and is positioned on the VV1 side of the boundary line B22 near to the VV2, as being a pixel related to the VV1. The image processing section 206 each of the pixels on choroidal vessels at a position of the area between the boundary line B21 and the boundary line B22 as being a pixel related to the VV1 and to the VV2. The two boundary lines B21, B22 may also be decided using a method combing graph cut processing and active contour processing.

Other than the method described above, there is also the following method as a method for setting overlapping areas as areas related to each of the VVs. As illustrated in FIG. 9B, for each of the VVs the image processing section 206 sets circles C1, C2 having radii of a specific length centered on the respective VV, and sets the circumference of each of the circles C1, C2 as a boundary line. For each pixel on a choroidal vessel not belonging to either the circle C1 or the circle C2, and for each pixel on a choroidal vessel within any overlapping area when the circle C1 and the circle C2 overlap, the image processing section 206 classifies the pixel as a pixel positioned in an overlapping area related to both the VV1 and the VV2. The image processing section 206 classifies each of the pixels on the choroidal vessels inside the circle C1 except for in any overlapping area as being a pixel related to VV1. The image processing section 206 classifies each of the pixels on the choroidal vessels inside the circle C2 except for in any overlapping area as being a pixel related to VV2.

Figure 10:
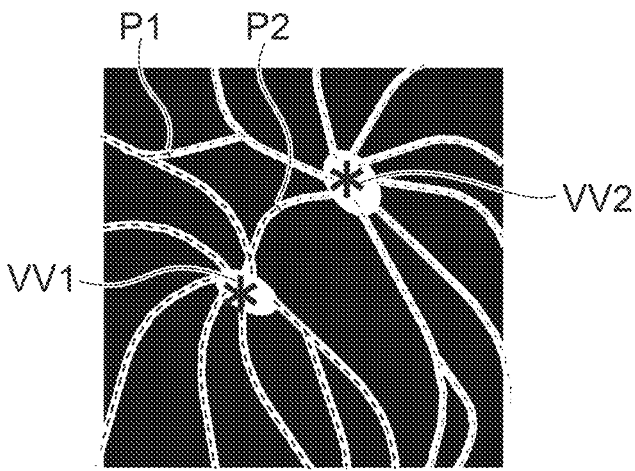
FIG. 10 is a diagram illustrating a choroidal vascular image of a part where adjacent VV1 and VV2 are present.

Next explanation follows regarding a method of classification by deciding boundary points on the choroidal vessels as the second classification method. FIG. 10 illustrates a choroidal vascular image of a part where the adjacent VV1 and VV2 are present. The image processing section 206 thins the lines of the choroidal vessels. The image processing section 206 counts the number of pixels along the thin-lined choroidal vessel to each of the VVs from each of the pixels on the thin-lined choroidal vessels. The image processing section 206 decides the VV that corresponds to the smallest number of pixels for each of the pixels, and associates the decided VV with the respective pixel. The image processing section 206 sets the pixels associated with the same VV as being in the same group. The image processing section 206 decides as boundary points P1, P2 positions between pixels where adjacent pixels on the thin-lined choroidal vessel belong to different groups. The image processing section 206 then, based on the boundary points P1, P2, classifies by deciding which (just a single) VV from out of the plural VVs each of the pixels on the choroidal vessels is related to.

Figure 11:
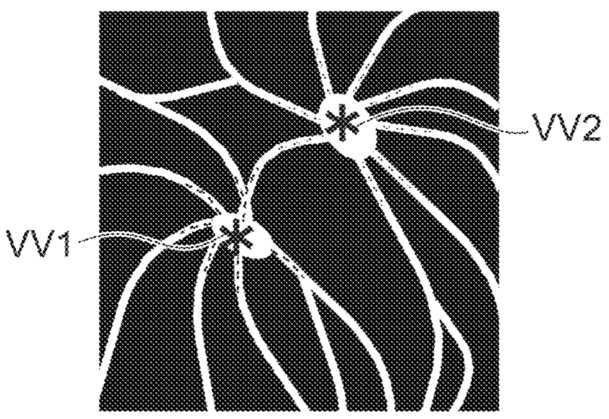
FIG. 11 is a diagram illustrating a choroidal vascular image of a part where adjacent VV1 and VV2 are present.

Next, description follows regarding a classification method without deciding boundary lines or boundary points as the third classification method. FIG. 11 illustrates a choroidal vascular image of a part where adjacent VV1 and VV2 are present. The image processing section 206 thins the lines of the choroidal vessels. For each of the pixels on the thin-lined choroidal vessels, the image processing section 206 counts the number of pixels along the thin-lined choroidal vessel to each of the VV1, VV2. The image processing section 206 then classifies each of the pixels for which the counted number of pixels along the thin-lined choroidal vessels is a specific number or greater from both the VV1 and VV2 as being a VV1, VV2-overlap pixel. The image processing section 206 classifies each of the pixels for which the counted number of pixels along the thin-lined choroidal vessel is less than the specific number as being a pixel corresponding to the VV to which the path is less than the specific number of pixels.

The blood vessel surface area computation processing proceeds to step 706 when one of the above classification processing has been completed.

At step 706, the image processing section 206 initiates a variable n for discriminating between each of the plural detected VVs to zero, then at step 708 the image processing section 206 increments the variable n by one.

Figure 12A:
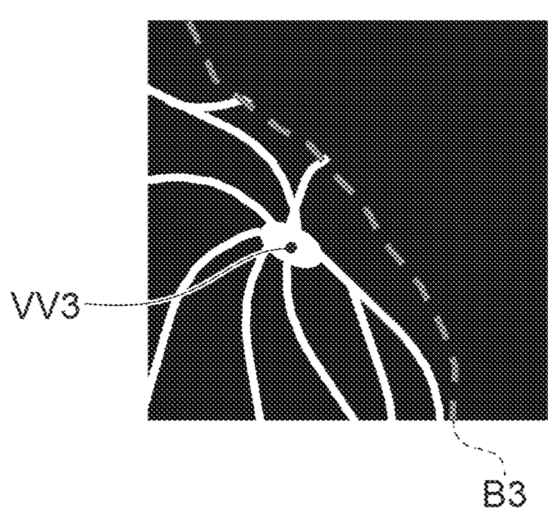
FIG. 12A is a diagram illustrating a choroidal vascular image of a part where a VV3 is present.
Figure 12B:
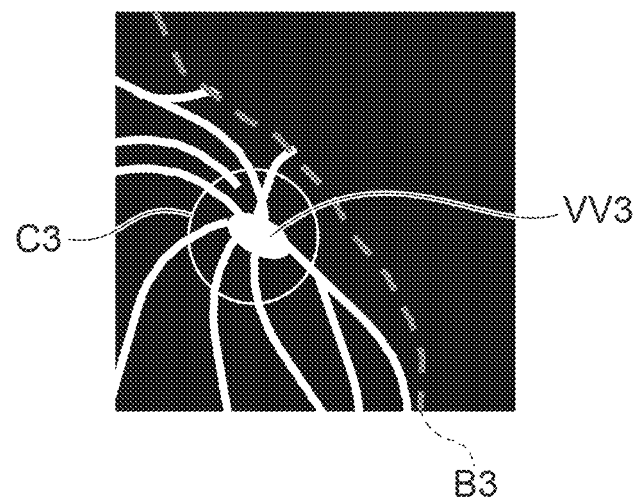
FIG. 12B is a diagram illustrating a choroidal vascular image of a part where a VV3 is present.

At step 710 the image processing section 206 extracts choroidal vessels joined (connected) to the VVn discriminated by the variable n, namely extracts connected blood vessels, as VVn-joined blood vessels. FIG. 12A and FIG. 12B illustrate choroidal vascular images of a part where a VVn (for example, VV3 (n=3) is present. The image processing section 206 may extract all the pixels of the choroidal vessels connected to the VVn (=3), however first, as illustrated in FIG. 12A, the image processing section 206 extracts only the portion of the pixels classified as pixels corresponding to VVn (=3) from out of the pixels of the choroidal vessels connected to the VVn (=3) in the choroidal vascular image. As illustrated in FIG. 12A, the image processing section 206 extracts choroidal vessels connected from the position of VVn (=3) (only the above classified pixels) as the VV-joined blood vessels.

Alternatively, the image processing section 206 may, as illustrated in FIG. 12B, extract choroidal vessels (only the above classified pixels) connected in a fixed range (circle C3 of a fixed length radius) from the VV3 position as the VVnjoined blood vessels.

Figure 13:
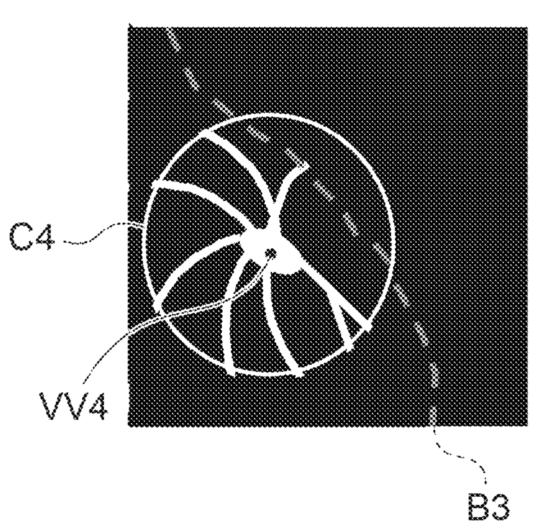
FIG. 13 is a diagram illustrating a choroidal vascular image of a part where a VV4 is present.

At step 712, the image processing section 206 extracts (identifies), from out of the VVnjoined blood vessels, only the choroidal vessels surrounding the VVn as VVn-surrounding blood vessels. FIG. 13 illustrates a choroidal vascular image of a part where a VVn (for example, VV4

(n=4)) is present. The image processing section 206 extracts, from the VVnjoined blood vessels, a remaining portion of blood vessel after removing a portion of blood vessel exceeding a fixed range (fixed length radius circle C4) from the VVn as VVn-surrounding blood vessels.

The choroidal vessels surrounding the VVn (VVn-surrounding blood vessels) are an example of a "choroidal vessel related to the vortex vein position" of the technology disclosed herein. The choroidal vessels surrounding the VVn (VVn-surrounding blood vessels) are connected to the VVn, and are an example of a "choroidal vessel connected to a vortex vein" of the technology disclosed herein.

At step 714 the image processing section 206 computes a surface area of the VVn-surrounding blood vessels. For example, for each pixel of the VVn-surrounding blood vessels, the image processing section 206 reads a fundus surface area corresponding to each of the pixels and computes the surface area of the VVn-surrounding blood vessels by adding up the read surface area for each of the respective pixels of the VVn-surrounding blood vessels. Note that the following value may be employed as the fundus surface area corresponding to the pixels. An eyeball model for the patient is built in advance by adjusting a standard eyeball model based on the eye axial length of the patient. A surface area on the patient eyeball model is associated with each pixel of the choroidal vascular image and stored in the storage device 254. At step 714, the image processing section 206 reads and employs the surface areas corresponding to the above pixels stored in the storage device 254.

At step 716 the image processing section 206 determines whether or not the variable n is equivalent to a total number N of detected VVs. Until the variable n is determined to be equivalent to the total number N, a VV for which the peripheral blood vessel surface area has not been computed remains, and so the blood vessel surface area computation processing returns to step 708 and the previous processing (from step 708 to step 716) is repeated.

The peripheral blood vessel surface area has been computed for all of the VVs when the variable n is determined to be equivalent to the total number N, and so the blood vessel surface area computation processing (step 606 of FIG. 6) is ended, and the image processing proceeds to step 608.

At step 608 the image processing section 206 executes analysis processing. Explanation follows regarding the analysis processing.

The image processing section 206 computes a statistical value of the blood vessel surface areas computed for all VVs. This statistical value is, for example, an average value and a standard deviation of the blood vessel surface areas computed for all VVs, and a maximum value and a minimum value from out of the blood vessel surface areas computed for all VVs.

The statistical value also encompasses an average value, standard deviation, maximum value, and minimum value of blood vessel surface area computed for each quadrant. Note that the image processing section 206 detects watersheds for the choroidal vascular network and defines the quadrants based on the detected watersheds. Note that the watersheds are areas in the choroidal vascular image where the density of choroidal vessels is lower than in other areas thereof (see, for example, curved lines LX, LY (see also the choroidal vascular image display field 544 of FIG. 14)).

The statistical value encompasses comparison values of the average value, standard deviation, maximum value, and minimum value for the blood vessel surface area between quadrants. The comparison values are differences of the values between each quadrant (average value, standard deviation, maximum value, and minimum value), a standard deviation, a maximum value, and a minimum value thereof.

The statistical value encompasses a VV center distance and VV center angle as set out below. Specifically, these values are found in the following manner. A graph is created to represent each position on the choroidal vascular image in polar coordinates (a distance and an angle from a center of the choroidal vascular image). Then, as a center position, at least one out of a centroid position of the VVs (from VV1 to VV4) or a weighted centroid position thereof is found, and a distance (VV center distance) from the center of the above graph to the center position and a center position angle (VV center angle) are found.

The image processing section 206 calculates a difference between the statistical values calculated above and corresponding statistical values pre-stored in a normal eye database stored in the storage device 254.

The image processing section 206 detects respective position of an optic nerve head and macular from UWF fundus images. The image processing section 206 computes a distance between the optic nerve head and each VV, a distance between the macular and each VV, angles formed between a line connecting the optic nerve head and the macular together and respective lines connecting the macular to each of the VVs, and angles formed between the line connecting the optic nerve head and the macular together and respective lines connecting the optic nerve head to each of the VVs.

The image processing section 206 computes a centroid position and a centroid position weighted by blood vessel surface area of each of the VVs as the center position for all VVs.

Figure 14:
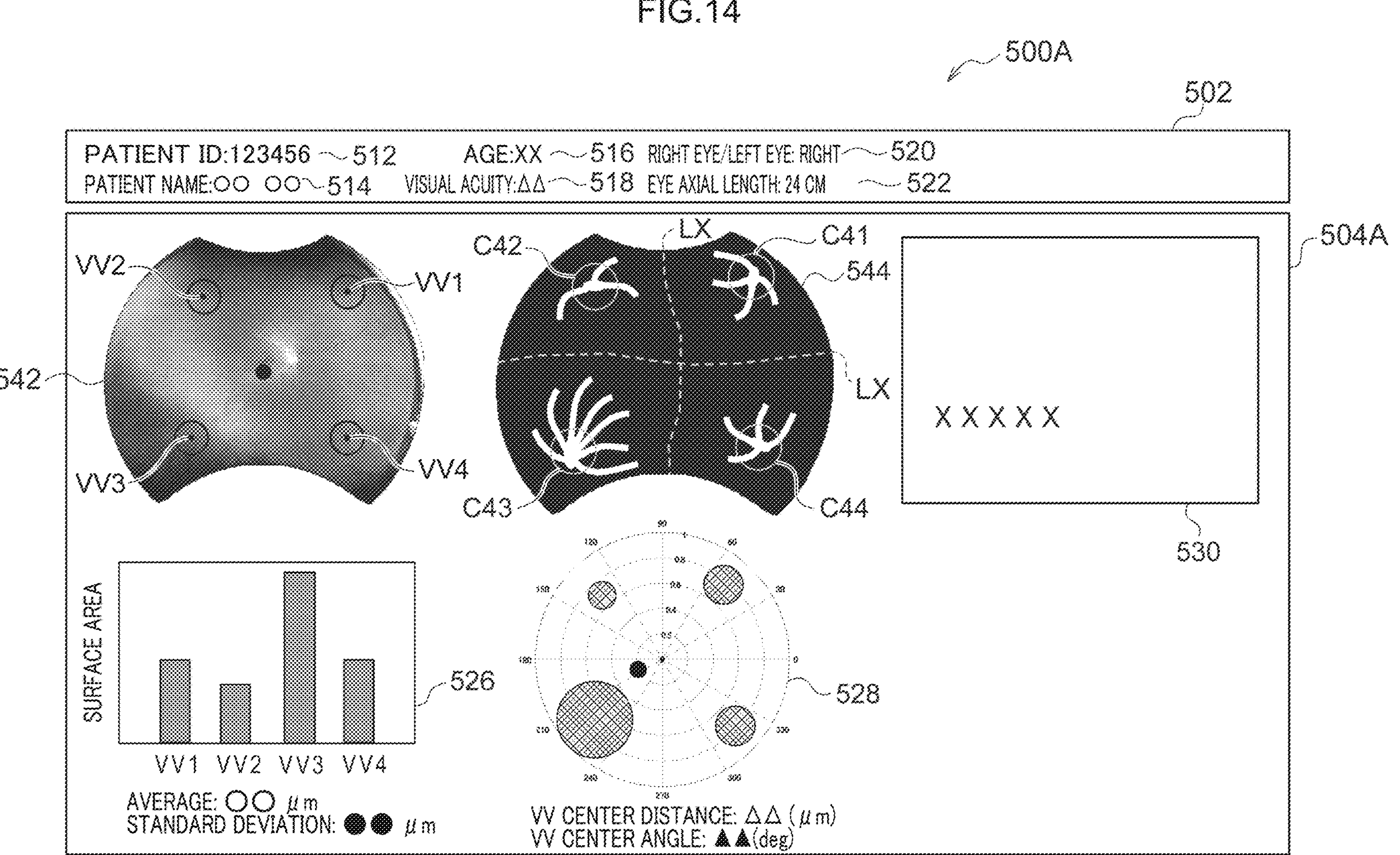
FIG. 14 is a schematic diagram illustrating a first display screen displayed on a display of a viewer.

At step 608, the image processing section 206 creates display screen data for displaying the above computed values. FIG. 14 illustrates a first display screen 500A. As illustrated in FIG. 14, the first display screen 500A includes an information area 502 and an information display area 504A. The information area 502 includes a patient ID display field 512, a patient name display field 514, an age display field 516, a visual acuity display field 518, a right eye/left eye display field 520, and an eye axial length display field 522. Based on the information received from the server 140 the viewer 150 displays each information in each of the respective display areas from the patient ID display field 512 to the eye axial length display field 522.

The information display area 504A is an area for displaying a fundus image or the like. Each of the following display fields is provided in the information display area 504A, specifically a comment field 530, a UWF fundus image display field 542, a choroidal vascular image display field 544, a first blood vessel surface area display field 526, and a second blood vessel surface area display field 528.

The comment field 530 is a free-form-input remark field where an ophthalmologist user is able to enter observation results or diagnosis results.

In the UWF fundus image display field 542, a circle (○) centered on the position of each VV (from VV1 to VV4) is displayed on a UWF fundus image, together with, as the center position, a circle area (●) centered on at least one from out of the centroid position or weighted centroid position, the weighted centroid position in the example of FIG. 14.

The choroidal vascular image display field 544 displays the curved lines LX, LY indicating each watershed, VV-joined blood vessels, and circles C4 (from circle C41 to circle C44) for setting the VVn-surrounding blood vessels so as to be displayed on the choroidal vascular image.

A bar graph indicating a blood vessel surface area corresponding to each of the VVs, and a blood vessel surface area average value: ○○(μm) and a standard deviation: ●●(μm) are displayed in the first blood vessel surface area display field 526. A specific value for the average blood vessel surface area is displayed in "○○". A specific value for the standard deviation is displayed in "●●".

The second blood vessel surface area display field 528 displays circles of area corresponding to the respective blood vessel surface areas centered on the position of each VV on a graph in which each position of the choroidal vascular image is represented in polar coordinates (a distance from the center of the choroidal vascular image and an angle), and displays, as the center position, at least one from out of the centroid position or the weighted centroid position. In the example illustrated in FIG. 14 a circle area (●) centered on the weighted centroid position is displayed.

The second blood vessel surface area display field 528 displays a distance (VV center distance: ΔΔ(μm)) of the center position (the weighted centroid position, for example) from the center of the above graph, and a center position angle (VV center angle: ▲▲ (deg)). A specific value of the VV center distance is displayed at ΔΔ(μm). A specific value of VV center angle is displayed at ♦▲(deg).

Processing of step 608 of FIG. 6 is ended when the creation of the display screen data described above has been completed, and at step 610 the image processing section 206 associates each of the values and the display screen data calculated at step 608 with the patient ID and outputs these to the storage device 254 (stores them therein).

Note that when an ophthalmologist is examining a patient, the patient ID is stipulated on the viewer 150 by operation of the ophthalmologist, and the viewer 150 instructs the server 140 to transmit the data stored in the storage device 254 associated with this patient ID. The server 140 transmits the various data stored in the storage device 254 associated with the patient ID to the viewer 150. The viewer 150 displays the first display screen 500A illustrated in FIG. 14 on a display based on the received data.

In the present exemplary embodiment the blood vessel surface area is calculated as described above. When disease occurs in choroidal vessels, there is an increase in the blood vessel surface area calculated for the VV corresponding to these choroidal vessels. This accordingly enables an ophthalmologist or the like to determine whether or not disease has occurred in the choroidal vessels of the VV from the VV blood vessel surface area. For example, in the example illustrated in FIG. 14 the VV3 blood vessel surface area is larger than the blood vessel surface area of other VVs. This accordingly enables an ophthalmologist or the like to determine whether or not there is a disease in the choroidal vessels of the VV3.

Moreover, in the present exemplary embodiment the unweighted centroid position is calculated, and also the weighted centroid position is calculated as the center position. For example, when a disease of blood flow concentrating at a single location occurs, the corresponding VV enlarges and the blood vessel surface area increases. This means that when the VV center point weighted by blood vessel surface area is computed, this weighted centroid position is shifted from the unweighted centroid position toward the side of the increased blood vessel surface area VV. This accordingly enables an ophthalmologist or the like to determine from the weighted centroid position and the unweighted centroid position whether or not a disease of blood flow concentrating at a single location has occurred.

In the exemplary embodiment described above, the position of the vortex veins (VVs) are detected as positions (X, Y) on the choroidal vascular image. However, the technology disclosed herein is not limited thereto. For example, a configuration may be adopted in which an eyeball model is derived by adjusting a standard eyeball model by the eye axial length stored associated with the patient ID, the choroidal vascular image is projected onto the derived eyeball model, and the positions of the vortex veins (VVs) are detected as positions (X, Y, Z) on the eyeball model onto which the choroidal vascular image has been projected. At step 608 of FIG. 6, each value is computed using the eyeball model onto which the choroidal vascular image has been projected.

For example, a position $v_n=(x_n, y_n, z_n)$ is computed for each of the VVs.

The center position $v_{center}$ for all the VVs is represented by a vector expressed by $v_{center}=R\times(x_{center}, y_{center}, z_{center})$. Herein R is a radius of the eyeball model adjusted by eye axial length of the examined eye.

$x_{center}$ is computed using the formula shown at Equation 1.

$$x_{center} = \frac{x_c}{\|x_c\|} \qquad \text{Equation (1)}$$

$$x_c = \frac{1}{\sum_{n=1}^{N} w_n} \sum_{n=1}^{N} w_n x_n$$

Herein: $x_{center}$ is a normalization of $x_c$, wherein $x_c$ is computed by taking a weighted mean of x; and $w_n$ is a weight related to blood vessel surface area. There is no limitation to finding a weighted mean in this manner, and an m-order mean or the like may be employed.

$y_c$ and $z_c$ are computed in a similar manner to $x_c$. $y_{center}$ and $z_{center}$ are also computed in a similar manner to $x_{center}$.

A vector from the eyeball model center toward the VV center point is computed by weighting each vector from the eyeball model center toward the respective VV by blood vessel surface area, and then combining these weighted vectors.

Figure 15:
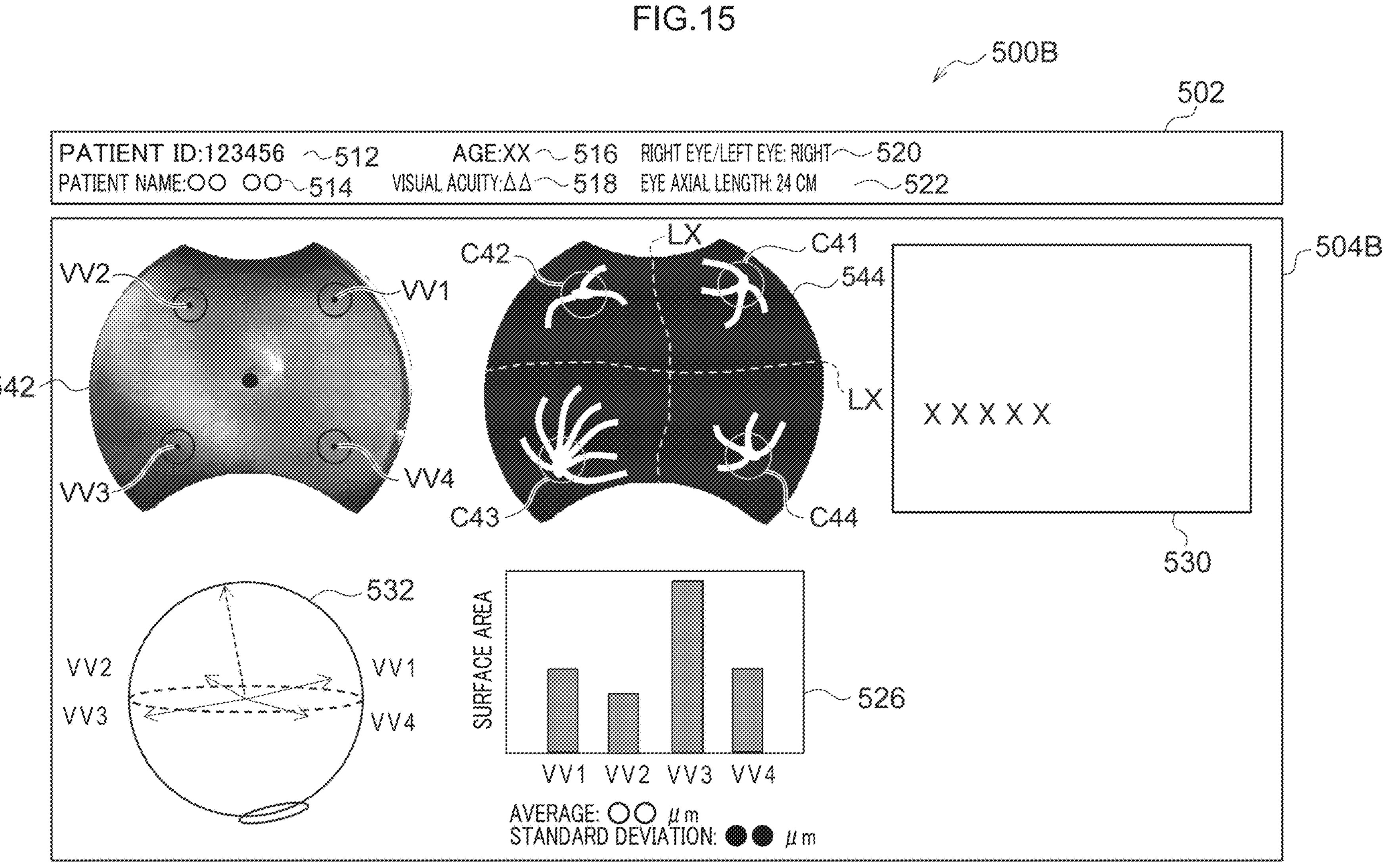
FIG. 15 is a schematic diagram illustrating a second display screen displayed on a display of a viewer.

FIG. 15 illustrates a case in which each of the values computed using the eyeball model at step 608 of FIG. 6 are displayed on a second display screen 500B. As illustrated in FIG. 15, the second display screen 500B is substantially the same as the first display screen 500A, and so explanation follows regarding differing parts thereof.

An eyeball model display field 532 is provided in the second display screen 500B instead of at least one out of the first blood vessel surface area display field 526 or the second blood vessel surface area display field 528 of the first display screen 500A. Note that in the example illustrated in FIG. 15 the eyeball model display field 532 is provided instead of the second blood vessel surface area display field 528. The eyeball model display field 532 is displayed with vectors to each VV (VV1 to VV4), and with a vector to at least one out of the centroid position or the weighted centroid position. A vector to the weighted centroid position is displayed in the example illustrated in FIG. 15.

Moreover, in the exemplary embodiment described above the choroidal vascular image obtained from the UWF fundus image is employed to calculate the blood vessel surface area. However, the technology disclosed herein is not limited thereto. For example, a volume image (three-dimensional image) based on OCT volume data may be employed so as to calculate a blood vessel volume. In such cases the blood vessel volume is employed at step 608 instead of the blood vessel surface area. For example, these blood vessel volumes may be employed as the above weights.

Although explanation has been given in the exemplary embodiments described above regarding an example in which a computer is employed to implement image processing using a software configuration, the technology disclosed herein is not limited thereto. For example, instead of a software configuration employing a computer, the image processing may be executed solely by a hardware configuration such as a field programmable gate array (FPGA) or an application specific integrated circuit (ASIC). Alternatively, a configuration may be adopted in which some processing out of the image processing is executed by a software configuration, and the remaining processing is executed by a hardware configuration.

Such technology disclosed herein encompasses cases in which the image processing is implemented by a software configuration utilizing a computer, and also image processing implemented by a configuration that is not a software configuration utilizing a computer, and encompasses the following technology.

First Technology

An image processing device including:

- an acquisition section that acquires a choroidal vascular image;
- a detection section that detects a vortex vein position from the choroidal vascular image;
- an identification section that identifies a choroidal vessel related to the vortex vein position; and
- a calculation section that calculates a size of the choroidal vessel.

Second Technology

An image processing method including:

- an acquisition section performing a step of acquiring a choroidal vascular image;
- a detection section performing a step of detecting a vortex vein position from the choroidal vascular image;
- an identification section performing a step of identifying a choroidal vessel related to the vortex vein position; and
- a calculation section performing a step of calculating a size of the choroidal vessel.

The image processing section 206 is an example of an “acquisition section”, a “detection section”, an “identification section”, and a “calculation section” of technology disclosed herein.

The following technology is proposed from the content disclosed above.

Third Technology

A computer program product for performing image processing, wherein:

- the computer program product includes a computer-readable storage medium that is not itself a transitory signal;
- a program is stored on the computer-readable storage medium; and
- the program causes a computer to execute:
  - a step of acquiring a choroidal vascular image;
  - a step of detecting a vortex vein position from the choroidal vascular image;
- a step of identifying a choroidal vessel related to the vortex vein position; and
- a step of finding a size of the choroidal vessel.

The server 140 is an example of a “computer program product” of technology disclosed herein.

It must be understood that the image processing described above is merely an example thereof. Obviously redundant steps may be omitted, new steps may be added, and the processing sequence may be swapped around within a range not departing from the spirit of the technology disclosed herein.

The entire content of the disclosure of Japanese Patent Application No. 2020-073123 is incorporated by reference in the present specification.

All publications, patent applications and technical standards mentioned in the present specification are incorporated by reference in the present specification to the same extent as if each individual publication, patent application, or technical standard was specifically and individually indicated to be incorporated by reference.

The invention claimed is:

1. An image processing method performed by a processor, the image processing method comprising:

- a step of acquiring a choroidal vascular image;
- a step of detecting positions of a first vortex vein and a second vortex vein from the choroidal vascular image; and
- a step of identifying a first pixel group associated with the first vortex vein and a second pixel group associated with the second vortex vein in the choroidal vascular image, based on a boundary line that is determined based on position information related to the first vortex vein and the second vortex vein, from pixels on a choroidal vessel.

2. The image processing method of claim 1, wherein:

- the step of identifying includes identifying the first pixel group based on the boundary line that is determined based on the direct distance from each pixel on the choroidal vascular image, to the first vortex vein, and to the second vortex vein.

3. The image processing method of claim 1, wherein:

- the step of identifying includes identifying the first pixel group based on the boundary line that is determined between the first vortex vein and second vortex vein based on a travel direction of the choroidal vessel.

4. The image processing method of claim 1, further including:

- a step of determining a surface area or volume of a choroidal vessel associated with the first vortex vein based on the first pixel group;
- wherein the step of determining a surface area or a volume includes determining, among the first pixel group, an area or a volume of the choroidal vessel associated with the first vortex vein based on pixels positioned within a fixed range containing a position of the first vortex vein.

5. The image processing method of claim 1, further including:

- a step of determining a surface area or a volume of a choroidal vessel associated with the first vortex vein based on the first pixel group; and
- a step of displaying a superimposed display of a surface area or a volume of the first vortex vein, which is determined in the step of determining a surface area or a volume, and a vein associated with the first vortex vein used to calculate the surface area or the volume.

6. The image processing method of claim 1, wherein:

- the step of acquiring the choroidal vascular image includes acquiring a three-dimensional image of a choroidal vessel which is based on OCT volume data; and the image processing method further includes the step of determining the volume of the choroidal vessel.

7. An image processing device comprising:

a memory and a processor coupled to the memory, wherein:

the processor is configured to execute:

a step of acquiring a choroidal vascular image;

a step of detecting positions of a first vortex vein and a second vortex vein from the choroidal vascular image; and a step of identifying a first pixel group associated with the first vortex vein and a second pixel group associated with the second vortex vein in the choroidal vascular image, based on a boundary line that is determined based on position information related to the first vortex vein and the second vortex vein, from pixels on a choroidal vessel.

8. A non-transitory storage medium storing a program executable by a computer to perform processing, the processing comprising:

a step of acquiring a choroidal vascular image;

a step of detecting positions of a first vortex vein and a second vortex vein from the choroidal vascular image; and a step of identifying a first pixel group associated with the first vortex vein and a second pixel group associated with the second vortex vein in the choroidal vascular image, based on a boundary line that is determined based on position information related to the first vortex vein and the second vortex vein, from pixels on a choroidal vessel.

* * * * *